(12) United States Patent
Millán et al.

(10) Patent No.: US 7,858,597 B2
(45) Date of Patent: Dec. 28, 2010

(54) PREPARATION OF FORMULATIONS OF ANGIOTENSIN II AT1 RECEPTORS ANTAGONISTS FOR THE TREATMENT OF ARTERIAL HYPERTENSION, OTHER CARDIOVASCULAR ILLNESSES AND ITS COMPLICATIONS

(75) Inventors: Rubén Dario Sinisterra Millán, Bairro Ouro Preto (BR); Robson Augusto Souza Dos Santos, Santa Amélia (BR); Fréderic Jean Georges Frezard, Cidade Jardim (BR); Washington Xavier De Paula, Barro Preto (BR)

(73) Assignee: Universidade Federal De Mimas Gerais - UFMG (BR)

( * ) Notice: Subject to any disclaimer, the term of this patent is extended or adjusted under 35 U.S.C. 154(b) by 0 days.

(21) Appl. No.: 10/474,640

(22) PCT Filed: Apr. 9, 2002

(86) PCT No.: PCT/BR02/00051

§ 371 (c)(1),
(2), (4) Date: Mar. 30, 2004

(87) PCT Pub. No.: WO02/080910

PCT Pub. Date: Oct. 17, 2002

(65) Prior Publication Data

US 2004/0171584 A1 Sep. 2, 2004

(30) Foreign Application Priority Data

Apr. 10, 2001 (BR) .................................... 0102252

(51) Int. Cl.
*A61K 31/724* (2006.01)
(52) U.S. Cl. ........................................................ 514/58
(58) Field of Classification Search .................... 514/58
See application file for complete search history.

(56) References Cited

U.S. PATENT DOCUMENTS

| | | | |
|---|---|---|---|
| 4,340,598 A | 7/1982 | Furukawa et al. | |
| 4,576,958 A | 3/1986 | Wexler | |
| 4,598,070 A | 7/1986 | Ohwaki et al. | |
| 4,666,705 A * | 5/1987 | DeCrosta et al. | 424/482 |
| 4,834,985 A | 5/1989 | Elger et al. | |
| 5,064,825 A | 11/1991 | Chakravarty et al. | |
| 5,073,641 A | 12/1991 | Bundgaard et al. | |
| 5,128,355 A | 7/1992 | Carini et al. | |
| 5,134,127 A * | 7/1992 | Stella et al. | 514/58 |
| 5,138,069 A | 8/1992 | Carini et al. | |
| 5,153,197 A | 10/1992 | Carini et al. | |
| 5,155,118 A | 10/1992 | Carini et al. | |
| 5,171,748 A | 12/1992 | Roberts et al. | |
| 5,210,079 A | 5/1993 | Carini et al. | |
| 5,256,687 A | 10/1993 | Becker et al. | |
| 5,266,583 A | 11/1993 | Ohtawa | |
| 5,472,954 A * | 12/1995 | Loftsson | 514/58 |
| 5,519,012 A | 5/1996 | Fercej-Temeljotov et al. | |
| 5,662,935 A * | 9/1997 | Motta | 424/465 |
| 5,728,402 A | 3/1998 | Chen et al. | |
| 5,756,546 A * | 5/1998 | Pirotte et al. | 514/605 |
| 5,834,432 A | 11/1998 | Rodgers et al. | |
| 5,859,258 A | 1/1999 | Breen et al. | |
| 5,916,883 A | 6/1999 | Shalaby et al. | |
| 6,087,386 A | 7/2000 | Chen et al. | |
| 6,096,772 A | 8/2000 | Fandriks et al. | |
| 6,178,349 B1 | 1/2001 | Kieval | |
| 6,204,256 B1 | 3/2001 | Shalaby | |
| 6,383,471 B1 * | 5/2002 | Chen et al. | 424/45 |

FOREIGN PATENT DOCUMENTS

| | | |
|---|---|---|
| AU | 200012728 A | 6/2000 |
| EP | 0253310 | 1/1988 |
| EP | 0500297 | 8/1992 |
| EP | 1153613 | 11/2001 |
| HU | 209658 | * 10/1994 |
| WO | WO 98/20044 | 5/1998 |

(Continued)

OTHER PUBLICATIONS

Ikeda et al, Journal of Controlled Release, 2000, 66, 271-280.*

(Continued)

*Primary Examiner*—Shaojia Anna Jiang
*Assistant Examiner*—Ganapathy Krishnan
(74) *Attorney, Agent, or Firm*—William J McNichol, Jr.; Reed Smith LLP

(57) ABSTRACT

Preparation of AT1 receptors antagonists formulations using the cyclodextrins, their derivatives and/or biodegradable polymers for the treatment of arterial hypertension, other cardiovascular disease and their complications. Until now, no applications using the $AT1_1$ receptor antagonists and cyclodextrins or derivatives and/or biodegradable polymers for the treatment of arterial hypertension, other cardiovascular diseases and their complications, was found in the technical state of art. The present invention is characterized by the combination of two different technologies: one is the molecular encapsulation of $AT1_1$ receptor antagonists in cyclodextrins and the other is the microencapsulation in biodegradable polymers. It also comprises the increase of the effectiveness of the $AT1_1$ receptor antagonists as well as an increase in their bio-availability. The present invention comprises a new more effective alternative for the treatment of arterial hypertension, other cardiovascular diseases and their complications.

31 Claims, No Drawings

FOREIGN PATENT DOCUMENTS

| WO | WO 99/16437 | 4/1999 |
|----|-------------|--------|
| WO | WO 00/37075 | 6/2000 |
| WO | WO 00/59475 | * 10/2000 |
| WO | WO 01/10851 | 2/2001 |

OTHER PUBLICATIONS

Gilding, D.K., Biodegradable Polymers, Biocompatibility of Clinical Implant Materials, Chapter 9, 1981, 209-231.*
Ruddy et al, Angiotensin II Receptor Antagonists, 1999, pp. 621-633.*
Uekama et al, Chem. Rev. 1988, 98, 2045-2076.*
Langer et al, J. Biomater. Sci. Polymer Edn. 1993, 3(4), 315-333.*
Gilding, Biodegradable Polymers, Biocompatibility of Clinical Implant Materials, 1981, Chapter 9, 209-231.*
The Merck Index 12th edition, 1996, p. 954, entry # 5613.*
Ruddy et al Angiotensin Receptor II Antagonists, 1999, pp. 621-633.*
Uekama et al Chem. Rev. 1998, 98, 2045-76.*
Gilding Biodegradable Polymers, Biocompatibility of Clinical Implant Materials, 1981, Chapter 9, 209-231.*
Langer et al J. Biomater. Sci. Polymer Edn. 1993, 3(4), 315-333.*
Kostis et al Angiotensin II Receptor Antagonists, 1999, 71, 621-633.*
The Merck Manual, 16$^{th}$ edition, 1992, pp. 409, 446-448, 498-500, 1450-1452, 1724.*
Uekama et al Journal of Controlled Release, 2000, 66, 271-280.*
Gilding , Biodegradable Polymers, Biocompatibility of Clinical Implant Materials, 1981, Chapter 9, 209-231.*
Uekama et al, (Chem. Rev. 1998, 98, 2045-76.*
Szejtli, Medicinal Research Reviews, 1994, 14(3), 353-62.*
Keipert et al, International J. Pharmaceutics, 1996, 142, 153-62.*
Hirayama et al, Pharmaceutical Sciences, 1995, 1 517-520.*
MacMahon, S. et al., Blood pressure, stroke, and coronary heart disease, Lancet 335:765-774, 1990.
Kannel, W.B. et al., Changing epidemiological features of cardiac failure, Br. Hear J 1994; 72 (suppl 3): S3-S9.
Oliveira, M.T. Clinical features and prognosis of patients with high congested heart failure, College of Medicine USP, 1999, considered english abstract only.
Kannel, W.B.; Blood pressure as a cardiovascular risk factor: prevention and treatment. JAMA 275:1571-1576, 1996.
The Fifth Report of the Joint National Committee on detection, evaluation, and treatment of High Blood Pressure. National Institute of Health; Arc, Intern, Med. 153:154-183, 1993.
Frohlich, E.D., Angiotensin converting enzyme inhibitors. Hypertension vol. 13, No. 5 (suppl I): 125-130, 1989.
Sasaki, K. et al., Cloning and expression of a complementary DNA enconding a bovine adrenal angiotensin II receptor type-1. Nature, 351:230-232, 1991.
Rey et al.; Report the Canadian Hypertension Society. Consensus Conference.3.Pharmacologic treatment of essential hypertension. Can. Med. Assoc. J. 157(9): 1245-1254, 1997; (3): 575-584, 1993.
Menard, J. Anthology of the renin angiotensin system: A one hundred reference approach to angiotensin II antagonists. J. Hypertension 11 (suppl 3): S3-S11, 1993.
Ganong, W. Neuropeptides in cardiovascular control. J. Hypertens 2(suppl 3): 15-22, 1984.
McIntyre, M. et al., Losartan, an orally active angiotensin Angiotensin II AT1 receptor antagonist: review of its efficacy and safety in essential hypertension. Pharmacol. Ther. 74(2):181-194, 1997.
Criscione, L. de Gasparo et al; Pharmacological profile of valsartan. Br. J. Pharmacol 110:761-771, 1993.
Shibouta, Y. et al; Pharmacological profile of a highly potent and long-acting angiotension II receptor antagonist, J. Pharmacol. Exp. Ther. 266:114, 1993.
Ruddy, Michael C. et al, Angiotensin II Receptor Antagonists. 71:621-633, 1999.
Fielitz, Activation of the Cardiac Renin-Angiotensin System and Increased Myocardial Collagen Expression in Human Aortic Valve Disease; Journal of the Amer. College of Cardiology; vol. 37, No. 5, Apr. 1999; 1443-9.
L. Szente and J. Szejtli, Highly soluble cyclodextrin derivatives, Adv. Drug Deliv. Rev. 36: 17-28, 1999.
Powell et al; A Review of the New Angiotensin II-Receptor Antagonist Irbesartan; Cardiovascular Drug Review; vol. 16, No. 3, 1998 pp. 169-194.
Tamada, et al; Review: The development of polyanhydrides for drug delivery applications; J. Biometer, Sci. Polymer Edn., vol. 3, No. 4, pp. 315-353; 1992.
Gilding; Biodegradable Polymers, Biocompatibility of Clinical Implant Materials; Chapter 9; pp. 209-231; 1981.
Wilson, P.W.; From hypertension to heart failure: what have we learned?; Clin Cardiol. 1999; Oct. 22; Suppl. 5VI-10; Abstract Only.
Lipkowitz et al., "Enantioselective Binding of Tryptophan by a-Cyclodextrin," (1992) J. Am. Chem. Soc., vol. 114, pp. 1554-1562.
Blaschke et al., "Enantiomer Separation of Drugs by Capillary Electromigration Techniques," (2000) J. Chromatography, vol. 875, pp. 3-25.

* cited by examiner

PREPARATION OF FORMULATIONS OF ANGIOTENSIN II AT1 RECEPTORS ANTAGONISTS FOR THE TREATMENT OF ARTERIAL HYPERTENSION, OTHER CARDIOVASCULAR ILLNESSES AND ITS COMPLICATIONS

This application is the U.S. national phase of international application PCT/BR02/00051 filed Apr. 9, 2002 which designated the U.S.

FIELD OF THE INVENTION

The present invention comprises the process of preparation of new formulations of ANGIOTENSIN II AT1 receptors antagonists, using the cyclodextrins or their derivatives, lipossomes and the biodegradable polymers for the treatment of arterial hypertension, other cardiovascular illnesses and its complications.

BACKGROUND OF THE INVENTION

In the majority of the countries in the world, from 15% to 25% of the adult population presents high arterial pressure (MacMahon, S. et al., Blood pressure, stroke, and coronary heart disease, Lancet 335:765-774, 1990). The cardiovascular risk increases with the level of arterial pressure: the higher the arterial pressure, the higher the risk of coronary occurrences. Hypertension, considered to be the main factor responsible for coronary, cerebral and vascular renal diseases, is the number one cause of death and incapacity among adults.

Heart failure is worldwide the main cause of hospitalization in the age group of 60 to 80 years of age. The ageing of the population alone is already a factor for the increase of its incidence: while 1% of the individuals present heart failure between the age of 25 to 54 years, among the elderly the incidence is much higher, reaching the level of 10% to those over 75 years of age (Kannel, W. B. et al., Changing epidemiological features of cardiac failure, Br. Hear J 1994; 72 (suppl 3):S3-S9).

Heart failure, owing to its clinical features, is a limiting disease which, with its aggravation, reduces the quality of life of the patients and, in the most serious cases, presents the characteristics of a malignant disease with a mortality rate of over 60% in the first year, even nowadays (Oliveira, M. T. Clinical features and prognosis of patients with high congested heart failure, College of Medicine USP, 1999). It is estimated that today, in the industrialized world alone, over 15 million people are affected by it and that only in the US, for example, the number of cases has increased 450% between 1973-1990 (Kannel, W. B. et al., Changing epidemiological features of cardiac failure, Br. Hear J 1994; 72 (suppl 3): S3-S9).

Hypertension is complex, multifactorial, of high prevalence, responsible for various deleterious effects and with high morbidity and mortality (Kaplan, N. M. Blood pressure as a cardiovascular risk factor: prevention and treatment. JAMA. 275:1571-1576, 1996). With the aim of improving the understanding of the disease, countless studies for the evaluation of the efficiency of its control in the general population and in special groups have been carried out. The control of blood pressure, without a wide non-medicament and/or pharmaceutical intervention in the associated risks factors (diabetes, obesity, tobacco), may reduce substantially the benefits of the long term treatment of arterial hypertension in the decrease of mortality (Wilson, P. W. et al., Hypertension. Raven Press. 94-114).

Hypertension is the pathology that most contributes to cardiovascular arteriosclerosis (The Fifth Report of the Joint National Committee on detection, evaluation, and treatment of High Blood Pressure. National Institute of Health (VJNC). Arch, Intem, Med. 153:154-181, 1994). According to statistics, one in every four americans is or will be hypertensive, and it is estimated that 4.78 millions of people have heart failure. Each year, 400 thousand new cases are diagnosed, giving rise to 800 thousand hospitalizations, with a cost of US$ 17.8 billions of dollars with the treatment.

In Brazil, data from SUS (Sistema Unificado de Saúde) have shown that in 1997, heart failure was the main cause of hospitalizations among the cardiovascular diseases, leading the government to spend R$ 150 million reais with its treatment, a number equivalent to 4.6% of all the expenses with health (Filho, Albanesi F. Heart failure in Brazil. Arq. Bras. Cardiol. 71:561-562, 1998).

The angiotensin II (Ang II), a potent vasoconstrictor, is the most important active hormone of the renin-angiotensin system (RAS) and it makes up an important determinant of the pathophysiology of hypertension. Ang II increases directly and indirectly the peripheral resistance. Directly, it produces vasoconstriction of small arteries and, to a lesser extent, at the level of the post-capillary venules, where a high number of ANGIOTENSIN II AT1 receptors is found. The constriction of the arteries mediated by Ang II increases the vascular resistance, which is a basic hemodynamic mechanism involved in the arterial pressure rise. The constricting intensity is higher in the kidneys and lower in the brain, lungs and in the skeletal muscle. Ang II also leads to the release of aldosterone by the supra-renal gland. The release of the aldosterone increases the blood volume through the increase of sodium and water reabsorption and of the excretion of potassium by the kidneys (Frohlich, E. D., Angiotensin converting enzyme inhibitors. Hypertension 13 (suppl I): 125-130, 1989). It is believed that this increases the arterial pressure in response to the increase of the cardiac output, the second basic hemodynamic mechanism in the rising of arterial pressure. It has been suggested that the release of catecholamines from the supra-renal medulla by Ang II and the stimulation of the release of the norepinefrine by the nerves terminals and the activation of the central nervous system leads to an increase of the sympathetic discharge. (Goodman and Gilman's, The Pharmacological Basis of Therapeutics $8^{th}$ ed. Pergamon Press, New York, p 755, 1990).

The RAS is an endocrine system in which the renin acts over the angiotensinogen of hepatic origin, to produce angiotensin I in plasma. This peptide is then converted to Ang II, through the action of the angiotensin-converting enzyme (ACE). Thereafter, Ang II is taken to its target organs by the blood flow, binding in a selective way to the ANGIOTENSIN II AT1 receptors (Sasaki, k. et al., Cloning and expression of a complementary DNA enconding a bovine adrenal angiotensin II receptor type-1. Nature, 351:230-233, 1991).

The treatment of hypertension aims not only the reduction of health care expenses, but also the prevention of target organs lesions, through changes in the quality of life and use of medication, when necessary (The Fifth Report of the Joint National Committee on detection, evaluation, and treatment of High Blood Pressure. National Institute of Health (VINC). Arch. Intem. Med.153:154-181,1994).

All the patients with systolic arterial pressure over 180 mmHg or diastolic arterial pressure over 110 mmHg must be submitted to pharmacological treatment, regardless of other present factors or not (Report the Canadian Hypertension Society. Consensus Conference.3. Pharmacologic treatment of essential hypertension. Xan. Med. Assoc. J. 149 (3):575-584, 1993).

Since the 60s, however, the anti-hypertensive drugs became an important tool in the treatment of high arterial pressure (Ménard, J. Anthology of the renin-angiotensin system: A one hundred reference approach to angiotensin II antagonists. J. Hypertension 11 (suppl 3): S3-S11, 1993). During the last four decades, the pharmacological research produced new types of drugs to treat hypertension: the diuretics in the 60s, the betablockers in the 70s, the calcium channel blockers and the angiotensin-converting enzyme inhibitors in the 80s and the ANGIOTENSIN II AT1 receptor antagonists in the 90s.

The ACE inhibitors (ACEI) are capable of inhibiting the conversion of the angiotensin I to Ang II. Thus, the vasoconstricting actions of Ang II are minimized. Preliminary studies showed that teprotide, the first inhibitor used clinically, has an anti-hypertensive action when administered by the intravenous route, however, is inactive by oral route. This fact strongly limited its use.

It is known today that ACE is a multi-action enzyme, which means that it acts on various substrates. Besides acting as a dipeptidase in angiotensin I and in bradykinin, it is capable of hydrolising several peptides, indicating that the enzyme can act in various tissues.

ACEI are excellent when administered in monotherapy. ACEI provokes a relatively fast drop of the arterial pressure in 60 to 70% of the patients with arterial hypertension (Ganong, W. Neuropeptides in cardiovascular control. J. Hypertens 2(suppl 3):1522,1984). They are generally well tolerated, but their use can bring about adverse side effects and reactions, some of which relatively serious, among them, angioneurotic edema and dry cough (8 to 10%).

The first attempt to develop antagonists of Ang II date from the beginning of the 70s and efforts were concentrated on the development of peptides analogous to Ang II, saralasine (1-sarcosina, 8-isoleucine angiotensin II) being the first one. However, these derivatives were not clinically acceptable as they also presented partial agonist activity. In 1982, the two first non-peptide antagonists of ANGIOTENSIN II AT1 receptor were developed (S-8307 and S-8308). However, in spite of being highly specific and without agonist activity, they presented weak binding to the Ang II receptors. With a series of changes in the molecular structure of these two precursors, a new potent product for oral use, and of high specificity was developed, losartan. Since then, many other non-peptide antagonists were developed, such as candesartan, irbersatan, valsartan, telmisartan, eprosartan, tasosartan and zolosartan.

Losartan is a molecule chemically described as a monopotassium salt of 2-butyl-4-cloro-1-[[2'-(1H-tetrazole-5-yl)[1,1'-biphenyl]-4-yl]methyl]-1H imidazole-5-ethanol. Its empirical formula is $C_{22}H_{22}ClKN_6O$, a crystal clear powder, white and pale, of free flow and molar mass of 461.01 g/mol. It is rapidly absorbed and it presents a bioavailability of 33% and the peak of maximum concentration is reached within one hour, with an half-life of about two hours. It is soluble in water, soluble in alcohol and slightly soluble in common organic solvents, such as acetonitrile and methyl-ethyl-cetone. Losartan reduces arterial pressure solely by a new, specific and selective mechanism of action: blockade of the Ang II receptor, regardless of the origin or way of production of the Ang II. Losartan does not block other hormone receptors, enzymes or important ionic channels in the cardiovascular regulation.

The oxidation of the 5-hydroxymetyl group in the imidazol ring results in the active metabolite of losartan, designated by EXP-3174. The mechanism of the singular action of losartan can be distinguished from the inhibition of the ACE, by measuring, in the plasma, the induced increase of the renin activity and of Ang II levels (Tavares, Agostinho et al, Antagonists of the Receptors of the Angiotensin II, Pharmacology and Cardiovascular Therapeutics, 305-315, 1998). During the administration of losartan, the renin activity is increased, leading to the increase of the Ang II in the plasma. After the discontinuity of the administration of losartan, the renin activity and the levels Ang II return to the levels of pretreatment. About 92% of an oral dose of losartan can be detected in the urine and in the feces; 5% are excreted with the losartan, 8% as EXP-3174 and the rest as inactive metabolites (Melntyre, M. et.al. Losartan, an orally active angiotensin ANGIOTENSIN II AT1 receptor antagonist: a review of its efficacy and safety in essential hypertension. Pharmacol. Ther. 74(2):181-194,1997).

Valsartan (1-oxopentyl-N'[[2'-(1H-tetrazole-5-yl)[1,1'-biphenyl]-4-yl]methyl]-L-vaniline) is a competitive antagonist of the receptor $AT_1$, presenting bioavailability of 25%, with an half-life of 9 hours, reaching the maximum peak in about 2 hours. It is minimally metabolized and excreted especially through the feces and only 15 to 20% appears in the urine (Criscione, L. de Gasparo et. al. Pharmacological profile of valsartan. Br. J. Pharmacol 110:761-771, 1993). If administered with Atenolol, Cimetidine, Digoxin, Furosemide, it presents pharmacokinetics interactions that enhanced its effect. Irbersartan (2-butyl-3-[[2'-(1H-tetrazole-5-yl)[1,1'biphenyl] 4-yl1,3-diazaspirol[4,4]-non-len-4-olone) is a competitive antagonist of the ANGIOTENSIN II AT1 receptor. It is metabolized essentially by oxidation, it presents a peak of concentration between 1.5 and 2 hours and an half-life around 11 to 15 hours (Nisato, D. A review of the new angiotensin II antagonist irbesartan. Cardiovasc Drug Rev). Its availability is of 60 to 80% and it is also excreted mostly by the bile (80%).

Candesartan (2-ethoxy-1-[[2'-(1H-tetrazole-5-yl)biphenyl-4-yl]methyl-1H-benzimidazole-7-carboxylic acid), presents high affinity for the ANGIOTENSIN II AT1 receptor and it dissociates slowly, presenting half-life of 9 hours, bioavailability of about 40% and it is eliminated mostly by the urine and the bile (Shibouta, Y. et. al. Pharmacological profile of a highly potent and long-acting angiotensin II receptor antagonist, J. Pharmacol. Exp. Ther. 266:114-120, 1993). When administered together with (nifedipine, digoxina or glibenclamide), it has presented better results.

Eprosartan ((E)-a-[[2-butyl-1-[(4-carboxyphenyl)metyl]-1H-imidazol-5-yl]methylene]-2-thiofenepropanoic acid), has also high affinity for the ANGIOTENSIN II AT1 receptor, with a bioavailability of 13 to 15%, with maximum concentration at about 2 hours. Approximately 90% is eliminated through the feces and the rest in the urine (Ruddy, Michael C. et. al. Angiotensin II Receptor Antagonists. 71:621-633, 1999).

Telmisartan (4'-[(1,4'-dimethyl]-2'propyl[2,6'-bi1H-benzimidazole]-1'-yl)methyl]1,1'biphenyl]-2-carboxilic acid) is a competitive inhibitor of the ANGIOTENSIN II AT1 receptor and presents a bioavailability of 45%. It is excreted mostly by the bile (97%) (Ruddy, Michael C. et. al. Angiotensin II Receptor Antagonists. 71:621-633, 1999).

The angiotensin-(1-7), (Asp-Arg-Val-Tyr-Ile-H is Pro), and its derivative $Sar^1$-Ang-(1-7) also antagonize the pressure effect of the Ang II in human beings (Ueda et al., Mol. Biol. Cell 11:259A-260A suppl. S December 2000) and rats. The contraction produced by Ang II in isolated arteries of rabbits and humans is also reduced by the angiotensin-(1-7) (Roks et al. Eur. Heart J 22:53-53 Suppl. S Sep, 2001).

U.S. Pat. No. 4,340,598 (CA1152515, JP56071073, EP0028833, DE3066313D), Yoshiyasu, Toyonara et al. (1982) have developed a method to obtain new anti-hypertensive compounds through the substitution of the imidazol ring by phenyl, halogen, nitro or amino groups, in order to obtain imidazol derivatives. These compounds presented an excellent antagonist activity for the ANGIOTENSIN II AT1 receptor, being utilized as hypotensive agents.

U.S. Pat. Nos. 4,576,958 (4,372,964), Wexler, Ruth R. (1986), has also developed some derivatives of the 4,5-diaryl-1H-imidazol-2-methanol, which presented anti-hypertensive effect, because of their vasodilating properties. This finding was based on a series of chemical reactions, among them, Friedel-Crafts acylation, reflux in formamide and oxidation.

U.S. Pat. No. 4,598,070 (CA1215359, DK 356684, EP135044, ES8506757, GR82322, JP60025967), Mashiro, Kawahara et al. (1986), have developed an invention based on the preparation of inclusion compounds between the anti-hypertensive agent, Tripamide, and cyclodextrins (cyclodextrin and cyclodextrin). The use of cyclodextrin resulted in the improvement of the solubility of tripamide.

U.S. Pat. No. 4,666,705, de Crosta, Mark. T. et al. (1987) have proposed a new drug-controlled release system for the treatment of hypertension. An inhibitor of ACE, the Captopril, was used because its fast absorption, with half-life of two hours. In order to prolong its presence in the organism, Captopril was associated to polymer or co-polymer in the form of tablets. The polymer utilized was the (polyvinyl pirrolidone) (PVP) and the technique used was the dry granulation. As a result, the drug permanence was increased from 4 to 16 hours.

U.S. Pat. No. 5,064,825, Chakravarty, Prasun, K. et al. (1991), have obtained new derivatives of the imidazol ring, presenting seven member-rings and showing antagonist activity for the ANGIOTENSIN II AT1 receptor.

U.S. Pat. No. 5,073,641, Bundgaard, Hans et al. (1991), have obtained new ester derivatives of the carboxylic acid as inhibitors to the ACE. Among them, the ethyl-ester, Pentopril, was found to be highly stable in the human plasma.

U.S. Pat. No. 5,171,748 (JP3005464, CA2017065, EP0399732), Roberts, David et al. (1992), have also obtained new heterocyclics derivatives of the imidazol ring, which antagonize the action of angiotensin II.

U.S. Pat. No. 5,256,687, Becker, Reinhard et. al. (1993), have claimed a pharmaceutical composition, consisting of an inhibitor of the ACE (Tandolpril or Pamipril) associated to a diuretic (Furosemide or Piretamide), and its use in the treatment of hypertension, this way increasing the efficiency of the ACE inhibitors.

U.S. Pat. No. 5,266,583, Otawa, Masakatsu (1993), have isolated a metabolite of the Losartan, which presented an antagonist activity for the ANGIOTENSIN II AT1 receptor.

U.S. Pat. No. 5,519,012, Fercej-Temeljoov, Darja et. al. (1996), have claimed a new inclusion compound for the anti-hipertensive agent, 1,4-dihydropiridine, with methyl-p-cyclodextrin and other derivatives such as cyclodextrin hydroxilate.

U.S. Pat. No. 5,728,402, Chen, Chih-Ming et al. (1998), have claimed the preparation and use of a pharmaceutical composition containing an internal phase, composed by Captopril (ACE inhibitor) and an hydrogel, and an external phase insoluble in the stomach. This formulation resulted in the increase of the duration of drug absorption.

U.S. Pat. No. 5,834,432, (AU5990796, CA2221730, EP0828505, WO09639164, JP115073625), Rodgers, Kathlen Elizabeth et al. (1998), utilized agonists of the $AT_2$ receptors to improve wound healing.

U.S. Pat. No. 5,859,258 (HR970565, CN124186, SK57099, EP0937068, AU5089898), Breen, Patrick et al. (1999), have developed a process for crystallizing the ANGIOTENSIN II AT1 receptor antagonist, Losartan through the addition of solvents (among them, isopropanol, water, cyclohexane) and followed by the distillation.

AU200012728-A, Anker, S D and Cats, Aj. S. (1999), have developed a new derivative of the imidazol ring, more efficient than Losartan when administered orally.

WO9916437, Remuzzi, Giuseppe (1999), have developed a new imidazol derivative. The resulting drug was capable of increasing the survival of patients with renal and cardiac transplants.

WO0110851, Galbiat Bárbara Via Goldomi (1999) et. al have developed a process for the preparation of lysine-carboxyanidride, an intermediate product in the synthesis of the Lisonopril.

WO0037075, Synthelabo, Elizabeth Sanofi et. al. (1999) claimed the use of a combination of an ANGIOTENSIN II AT1-receptor antagonist (Irbesartan) and an immunosupressor (cyclosporin). This combination was found to be efficient in the treatment of cardiovascular problems.

U.S. Pat. No. 6,087,386 (WO9749392A1) Chen, Tzyy-Show H. et al. (2000) claimed the preparation an use of a pharmaceutical containing one layer of Losartan (ANGIOTENSIN II AT1 receptor antagonist) and the other layer of maleate de enalapril (ACE inhibitor). This formulation resulted in the improvement of the pharmacological action, decreasing the side effects and prolonging the absorption.

U.S. Pat. No. 6,096,772 (AU1184097, AU706660, CA2225175, HU9901448, CN1192681, JP11507921T, ZA9604690), Fandriks, Lars et al utilized ANGIOTENSIN II AT1 receptor antagonists for the treatment or prophylaxis of dispeptidic symptoms.

U.S. Pat. No. 6,178,349, Kieval, Roberts S. et al. (2001) have developed a device based on the release of the drug via neural stimulation for the treatment of cardiovascular diseases. This device consists of an eletrode connected to the nerve, an implantable pulse generator and a reservoir which contains the drug to be applied. During the use, the electrode and the release of the medicine stimulate the nerve, which affects the control over the cardiovascular system.

DETAILED DESCRIPTION

Various processes have been developed in order to obtain more efficient and/or less toxic drugs for the treatment of arterial hypertension. This is evident from the large number of patents identified in the technical state of art. However, these processes still present serious side effects, and the resulting drugs often exhibit short half-life and low bio-availability. The present finding, heron, comprises the preparation and use of controlled-release systems for the ANGIOTENSIN II AT1-receptor antagonists, using cyclodextrins and their derivatives which increase the drug half-life from 9 to 60 hours, resulting in an increase of the bioavailability of the antagonists in the biological system. This means that the resulting formulations presents a great potential as alternative drugs to be used in the treatment of hypertension in warm blood animals.

A particular drug could be chemically modified in order to alter its properties such as biodistribution, pharmacokinetics and solubility. Various methods have been used to increase the solubility and stability of drugs, among them the use of organic solvents, their incorporation within emulsions or liposomes, the adjustment of pH, their chemical modifications and their complexation with the cyclodextrins.

The cyclodextrins are oligosacharides cyclic family, which include six, seven or eight units of glucopyranose. Due to sterics interactions, the cyclodextrins, CD's, form a cycle structure in the shape of a (cone truncado) with an internal cavity apolar. Those are compounds chemically stable that can be modified in a regioselective way. The cyclodextrins hosts form complexes with various hydrophobic guests in their cavity. The CD's have been used for the solubilization and encapsulation of the drugs, perfumes and fragrances as described by Szejtli, J., Chemical Reviews, (1998), 98, 1743-1753. Szejtli, J., J. Mater. Chem., (1997), 7, 575-587.

According to detailed studies of toxicity, mutagenecity, teratogenecity and carcinogenecity about the cyclodextrins, described in [Rajewski, R. A., Stella, V., J. Pharmaceutical Sciences, (1996), 85, 1142-1169], these are presented with low toxicity specially of the (hidroxypropyl-β-cyclodextrin, as reported in Szejtli, J. Cyclodextrins: properties and applications. Drug investing., 2(suppl. 4):11-21, 1990. Except for some high concentrations of some derivates which cause harm to the eritrocites, these products in general are not harmful to the health. The use of cyclodextrins as aditives in foods has already been authorized in countries such as Japan and Hungary, and for more specific applications, in France and Denmark. Besides this, they are obtained from a renewable source of degradation of the amide. All these characteristics are a high motivation for the research findings of new applications. The structure of the molecule of CD is similar to a cone truncate one, of Cn approximately simmetry. The primary hydroxilas are located in the narrowest side of the cone by the connections of hydrogen intramoleculars, this element is flexible enough to allow a considerable deviance in the regular shape.

The known cyclodextrin derivatives can be classified according to their polarity, size, biological activity, etc. As for their practical uses are classified as follows: 1. Carriers (solubilizers, stabilizers) for biologically active substances; 2. Enzyme models; 3. Separating agents (for chromatography or batch-processes); 4. Catalysts and additives (as detergents, viscosity modifiers, etc), L. Szente and J. Szejtli, Adv. Drug Deliv. Rev. 36 (1999), 17. The CD's are moderately soluble in water, methanol and ethanol and readily soluble in polar solvents, such as the dimetyl sulfoxide, dimetylformamide, N,Ndimetylacetamide e piridine.

Numerous research works exist in the literature about the effects of the increase of solubility in water of the guests little soluble in water, using the cyclodextrins through the using compounds of inclusion were describe in Szejtli, J., Chemical Reviews, (1998), 98, 1743-1753. Szejtli, J., J. Mater. Chem., (1997), 7, 575-587.

In order to design a drug delivery system (DDS) various kinds of high performance carrier materials are being developed to deliver the necessary amount of drug to the targeted site for a necessary period of time, both efficiently and precisely.

Cyclodextrins, biodegradable or non biodegradable polymers, liposomes, emulsions, multiple emulsions are potential candidates for such a role, because of their ability to alter physical, chemical, and biological properties of guest molecules Besides the cyclodextrins, a number of drug delivery systems have been investigated, including polymer microcapsules, microparticles, liposomes and emulsion. Many of these are prepared from synthetic biodegradable polymers such as polyanhydrides and poly(hydroxy acids). In these systems the drugs incorporate in a polymeric microspheres, which release the drug inside the organism, in small and controlled daily doses, during days, months or until years.

Several polymers already were tested in controlled release systems. Such as: polyuretans for its elasticity, polysiloxans or silicons for being a good one insulating, polymethylmetacrilate for its physical force, polyvinilalcohol for its hydrofobicity and resistance, polyethilene for its hardness and impermeability (Gilding, D. K. Biodegradable polymers. Biocompat. Clin. Impl. Mater. 2:209-232, 1981). Biodegradable polymers and biocompatible polymers, hve been extensively investigated as vehicle for controlled release systems due to their ability to undergo surface degradation. These kind of polymers can be chose from: poly(2-hidroxi-ethylmetacrilate), polyacrilamide, polymer from lactic acid (PLA), from glicolic acid (PGA), and the respective ones co-polymers, (PLGA) and the poly(anidrides), as described by Tamada and Langer, J. Biomater. Sci. Polym. Edn, 3(4):315-353.

A formulation of the present invention can also include other components such as a pharmaceutical acceptable excipient. For example, formulation of the present invention can be formulated in an excipient that the animal to be protected can tolerate. Excipients can also contain minor amounts of additives, such as substances that enhance isotonicity and chemical stability of buffers. Standard formulation can either be liquid injectables or solids which can be taken up in a suitable liquid as a suspension or solution for injection or oral formulation. Suitable controlled release vehicles include, but are not limited to, biocompatible polymers, other polymeric matrices, capsules, microcapsules, nanocapsules, microparticles, nanoparticles, bolus preparations, osmotic pumps, diffusion devices, liposomes, lipospheres and transdermal delivery systems, implantable or not.

In the last years, several systems of drugs delivery systems have been studied to improve the drug absorption, to increase the drug stability and target it to a certain cell population. These studies led to the development of several products based on cyclodextrins, emulsions, liposomes and polymers for drug carrying and deliverying. These formulations can be administered through intramuscular, intravenous, subcutaneous injection, oral application, inhalation or devices that can be implanted.

Until now, no application using the ANGIOTENSIN II AT1 receptor antagonists, the cyclodextrins or their derivatives, lipossomes and the biodegradable polymers and combinations thereof has been found in the technical state of the art for the treatment of arterial hypertension or other cardiovascular diseases, such as the heart failure in warm blood animals. This characterizes the present invention as a novel more effective alternative for the treatment of these pathologies and their complications.

The present invention is characterized by the combination of two different technologies: one is the molecular encapsulation of ANGIOTENSIN II AT1 receptor antagonists in cyclodextrins and/or lipossomes and the other is the microencapsulation in biodegradable polymers. It is also characterized by the increase of the effectiveness of the ANGIOTENSIN II AT1 receptor antagonists as well as by an increase in their bioavailibility.

In addition, the present invention represent the increase hypotensor effect of the ANGIOTENSIN II AT1 receptors antagonists associated with cyclodextrins and the ones biodegradable polymers.

The present invention can be better understood by some of the following examples, but are not limited.

EXAMPLE 1

Preparation of the Inclusion Compounds Between β-cyclodextrin and ANGIOTENSIN II AT1 Receptors Antagonists: Losartan as Example The preparation is made in equimolar proportions of cyclodextrin and AT1 receptors antagonists. In briefly, β-cyclodextrin and/or its derivatives is dissolved in water using stirring and heating. Then the respective amount of losartan is added to the aqueous solution. Following the dissolution, the mixture is frozen in liquid nitrogen and submitted to the lyophilization process, obtaining a dry solid. The solid obtained is then submitted to the physical-chemistry characterization using the spectroscopy absorption in Infrared range, thermal analysis (TG/DTG and DSC) and X-ray diffraction. In the infrared spectra of the β-cyclodextrin bands were observed around $3500\ cm^{-1}$, $v_{OH}$, in $2910\ cm^{-1}$, $v_{CH3}$ asymmetric, and in $1440\ cm^{-1}$, $v_{C=O}$. For the losartan bands were verified around $3400\ cm^{-1}$ corresponding to the $v_{NH}$, in $2980\ cm^{-1}$, $v_{CH3}$ asymmetric, in $2770\ cm^{-1}$, $v_{CH3}$ symmetric, around $1600\ cm^{-1}$, $v_{C=C}$ of aromatic, around $1350\ cm^{-1}$, $v_{CH}$, in $1500$-$1600\ cm^{-1}$ associated to the combination of the manners vibrational $v_{C=C+C=N}$, and in $760\ cm^{-1}$ a strong band corresponding to the movement CH3 'rock'. In the IR spectra of the inclusion compound the absence of the bands of CH3 'rock', $v_{C-H}$ symmetrical in $2770\ cm^{-1}$ and $v_{N-H}$ in $3400\ cm^{-1}$, and decrease of the bands in $1500$-$1600\ cm^{-1}$ associated to the modes of the imidazolic and aromatic rings. These observations evidence the formation of the inclusion compound.

The curves TG/DTG of β-cyclodextrin presented two decompositions stages, one around 85° C., due to the loss of seven molecules of water included in the cavity, and other around 320° C., corresponding to the decomposition of the substance, this resulted is reinforced through the respectively DSC curves. The curves TG/DTG for the Losartan presented three decompositions, being first around 110° C. corresponding a loss of water, another one around 190° C. indicating the melting of the material and a third around 400° C., where it happens total decomposition of the losartan. Curve TG of the inclusion compound shows an increase of the thermal stability when compared to the pure losartan. On the other hand in the same TG curve two thermal decompositions events are observed, being the first around 60° C., corresponding to the loss of three molecules of water and another one in about 300° C., due to the total decomposition of the supramolecular compound.

X-ray patttern diffraction of inclusion compound presented new crystalline phases, when observed the XRD pattern of the β-cyclodextrin presented main peaks in 4, 12 e 25° 2θ, the XRD pattern of the Losartan in 11, 15.2, 19, 23 and 29.2° 2θ, while the XRD pattern of the inclusion compound presented a more amorphous profile with the disappearance of peaks in 4, 23 and 25° 2θ and appearance of new peaks in 6 and 15° 2θ.

EXAMPLE 2

Preparation of the Inclusion Compound Between Hydroxypropil-β-cyclodextrin and the ANGIOTENSIN II AT1 receptors antagonists: losartan as example.

The preparation was prepared in a molar ratio 1:1, Hydroxypropil-β-cyclodextrin and the ANGIOTENSIN II AT1 receptors. In briefly, Hydroxypropil-β-cyclodextrin and/or its derivatives is dissolved in water using stirring and heating. Then the respective amount of losartan is added to the aqueous solution. Following the dissolution, the mixture is frozen in liquid nitrogen and submitted to the lyophilization process, obtaining a dry solid. The solid obtained is then submitted to the physical-chemistry characterization using the spectroscopy absorption in Infrared range, thermal analysis (TG/DTG and DSC) and X-ray diffraction. The Infrared spectra of the hydroxypropil-β-cyclodextrin presented absorption bands in $3400\ cm^{-1}$, $v_{O-H}$, around $2900\ cm^{-1}$, $v_{C-H}$, in $1140\ cm^{-1}$, $v_{C-O-C}$ and in $1630\ cm^{-1}$, $v_{OH}$. In the IR spectra of the inclusion compound is verified the absence of the bands of CH3 'rock', $v_{C-H}$ symmetrical in $2770\ cm^{-1}$ and $v_{N-H}$ in $3400\ cm^{-1}$, which evidence the formation of the inclusion compound.

The curves TG/DTG for the hydroxypropil-β-cyclodextrin shown a loss of mass around 60° C. associated to the loss of two water molecules. Soon after, it happens a thermal stability to approximately 300° C., when the sample suffers complete decomposition. The same phenomena was verified in the DSC curve, where it was observed a exothermic peak at 367° C., indicating decomposition of the material. The TG/DTG curve of the inclusion compound shown two decomposition process. Being the first around 100° C. corresponding to the loss of three molecules of water and another in about 300° C. due to the total decomposition. It is still verified an increase of the thermal stability of guest after inclusion.

The X-ray pattern diffraction of the inclusion compound presented new crystalline phases, when compared to the X-ray pattern of the hydroxypropil-β-cyclodextrin, which it shown as amorphous substance. The X-ray pattern of the Losartan presented peaks in 11, 15.2, 19, 23 and 29.2° 2θ.

EXAMPLE 3

Preparation of the Microspheres in the Basis of Biodegradable Polymer (PLGA) and the Inclusion Compound Obtained from Example 1 and 2

Firstly a emulsion constituted of an organic phase constituted of poli(acid lactic-glycolic) (PLGA) dissolved in dichloromethane and an aqueous phase constituted of the antagonist of ANGIOTENSIN II AT1 receptors, as the losartan for example is prepared. That emulsion is then submitted to the sonication for half minute and is added to 1% (PVA) solution, forming a second emulsion, which suffers stirring for 1 minute to complete homogenization of the microemulsion. The system is maintained under stirring without heating for 2 hours until the evaporation of the solvent. The mixture is centrifuged by 2 to 3 times, and washed three times with water to remove the surface-adsorbed PVA and finally resuspended in 2 mL of water and freeze-dried. Then the solid microspheres were characterized through the thermal analysis and scanning electron microscopy SEM. The microspheres DSC curve shown a vitreous transition similar to which it was observed to the PLGA polymer. The respectively SEM micrographs shown 50 microns of particles size. It is still verified the porous surface of the microspheres. To determine the capacity of encapsulation of the different used systems calibration curves they were built through the UV-VIS spectroscopy obtaining a relationship between concentration and absorbance, and thus was determined the amount of losartan incorporated (see Table 1).

TABLE 1

Percentage of encapsulation of the different used systems

| System | Percentage of encapsulation |
| --- | --- |
| losartan + PLGA | 36.7% |
| losartan + HP-βCd + PLGA | 72.0% |
| losartan + βCd + PLGA | 85.0% |

HP-βCd (hydroxypropil-β-cyclodextrin)
PLGA (poly(acid lactic-glicolic)
βCd (β-cyclodextrin)

From data of Table 1 was verified the great differences among the values of encapsulation percentage. This fact is due to the different solubilities of losartan, β-cyclodextrin and of the hydroxypropil-β-cyclodextrin, and the β-cyclodextrin presents smaller solubility, presenting larger encapsulation percentage.

EXAMPLE 4

Comparison of the Effect of Losartan Included in β-cyclodextrin and HP-β-cyclodextrin in the Pressor Effect of in Ang II in Rats Rats with cateters implanted in the femoral artery and femoral vein were submitted to the injection of graded doses of Angiotensina II (5, 10 and 20 ng/100 µL) before and 2, 6, 24 and 48 hours after the losartan administration (0.2 mg/Kg) and losartan included in cyclodextrin (gavage). The losartan included in cyclodextrins blocked in approximately 75% the pressor effect of Ang II for up to 48 hours. Losartan alone blocked the effect of Ang II for about 8 hours

EXAMPLE 5

Comparison of the Effect of Losartan with Losartan Incorporated in Biodegradable Polymer in the Pressor Effect of Ang II in Rats Male rats weighing (330-350 g) instrumented for telemetric recording of arterial pressure (Data Science System) were anesthetized and submitted to the implantation of cateters in the femoral vein. Injections of Ang II (5, 10 and 20 ng/100 µL) they were done before and after the subcutaneous injections of losartan (0.7 mg), losartan incorporated in biodegradable polymers containing 0.7 mg of the drug or polymer only. Injections of Ang II were made after 2, 8 and 24 hours and then at intervals of 24 hours, for 15 days. Significant blockade of the pressor effect of Ang II with the combination biodegradable polymer-losartan-β-cyclodextrin could be demonstrated for up to 15 days. No significant changes were observed with the vehicle administration. Losartan alone blocked the Ang II effect for about 8 hours.

We claim:

1. A composition comprising an inclusion compound consisting essentially of water-soluble losartan and a hydrophilic cyclodextrin chosen from β-cyclodextrin or hydroxypropyl-β-cyclodextrin.

2. The composition according to claim 1, wherein the water-soluble losartan is losartan monopotassium salt.

3. The composition according to claim 1, wherein the cyclodextrin is β-cyclodextrin.

4. The composition according to claim 1, wherein the cyclodextrin is hydroxypropyl-β-cyclodextrin.

5. The composition according to claim 1, wherein the composition is a controlled-release system.

6. The composition according to claim 1, wherein the composition shows an approximately 6-fold increase in the duration of the effect of the water-soluble losartan in comparison to water-soluble losartan alone.

7. The composition according to claim 1, wherein the half-life of water-soluble losartan is increased.

8. A composition comprising an inclusion compound consisting essentially of water-soluble losartan and a hydrophilic cyclodextrin chosen from β-cyclodextrin or hydroxypropyl-β-cyclodextrin, wherein the composition further comprises a biodegradable or biocompatible polymer that encapsulates the inclusion compound.

9. The composition according to claim 8, wherein the polymer has a degradable surface.

10. The composition according to claim 8, wherein the polymer is chosen from poly(2-hydroxyethyl methacrylate), polyacrylamide, poly(lactic acid) (PLA), poly(glycolic acid) (PGA), poly(lactic-glycolic acid) (PLGA), and poly(anhydrides).

11. The composition according to claim 8, wherein the composition is a controlled-release system.

12. The composition according to claim 8, wherein the half-life of water-soluble losartan is increased.

13. A process for the preparation of a composition according to claim 1 comprising forming an inclusion compound between water-soluble losartan and a hydrophilic cyclodextrin chosen from β-cyclodextrin or hydroxypropyl-β-cyclodextrin.

14. A process for the preparation of a composition according to claim 8 comprising forming an inclusion compound between water-soluble losartan and a hydrophilic cyclodextrin chosen from β-cyclodextrin or hydroxypropyl-β-cyclodextrin and encapsulating the inclusion compound with a biodegradable or biocompatible polymer.

15. The process of claim 14, wherein the polymer has a degradable surface.

16. A pharmaceutical composition comprising the composition as claimed in claim 1 and a pharmaceutical acceptable diluent or excipient.

17. The pharmaceutical composition according to claim 16, wherein the composition is for oral, intramuscular, intravenous, subcutaneous or inhalation administration.

18. The pharmaceutical composition according to claim 16, wherein the composition is solid or liquid.

19. The pharmaceutical composition according to claim 16, wherein the composition has an improved bioavailability in comparison with the pharmaceutical composition without a hydrophilic cyclodextrin chosen from β-cyclodextrin or hydroxypropyl-β-cyclodextrin.

20. A method of treating arterial hypertension comprising administering to a patient in need thereof a therapeutically effective amount of at least one pharmaceutical composition of claim 16.

21. A method of treating arteriosclerosis associated with arterial hypertension comprising administering to a patient in need thereof a therapeutically effective amount of at least one pharmaceutical composition of claim 16.

22. A pharmaceutical composition comprising the composition as claimed in claim 8 and a pharmaceutical acceptable diluent or excipient.

23. The pharmaceutical composition according to claim 22, wherein the composition is for oral, intramuscular, intravenous, subcutaneous or inhalation administration.

24. The pharmaceutical composition according to claim 22, wherein the composition is solid or liquid.

25. The pharmaceutical composition according to claim 22, wherein the composition has an improved bioavailability in comparison with the pharmaceutical composition without a hydrophilic cyclodextrin chosen from β-cyclodextrin or hydroxypropyl-β-cyclodextrin.

26. A method of treating arterial hypertension comprising administering to a patient in need thereof a therapeutically effective amount of at least one pharmaceutical composition of claim 22.

27. A method of treating arteriosclerosis associated with arterial hypertension comprising administering to a patient in need thereof a therapeutically effective amount of at least one pharmaceutical composition of claim 22.

28. A method of treating stroke associated with arterial hypertension comprising administering to a patient in need thereof a therapeutically effective amount of at least one pharmaceutical composition of claim 16.

29. A method of treating stroke associated with arterial hypertension comprising administering to a patient in need thereof a therapeutically effective amount of at least one pharmaceutical composition of claim 22.

30. An inclusion compound consisting essentially of losartan monopotassium and β-cyclodextrin.

31. An inclusion compound consisting essentially of losartan monopotassium and hydroxypropyl-β-cyclodextrin.

* * * * *